Figure 1:
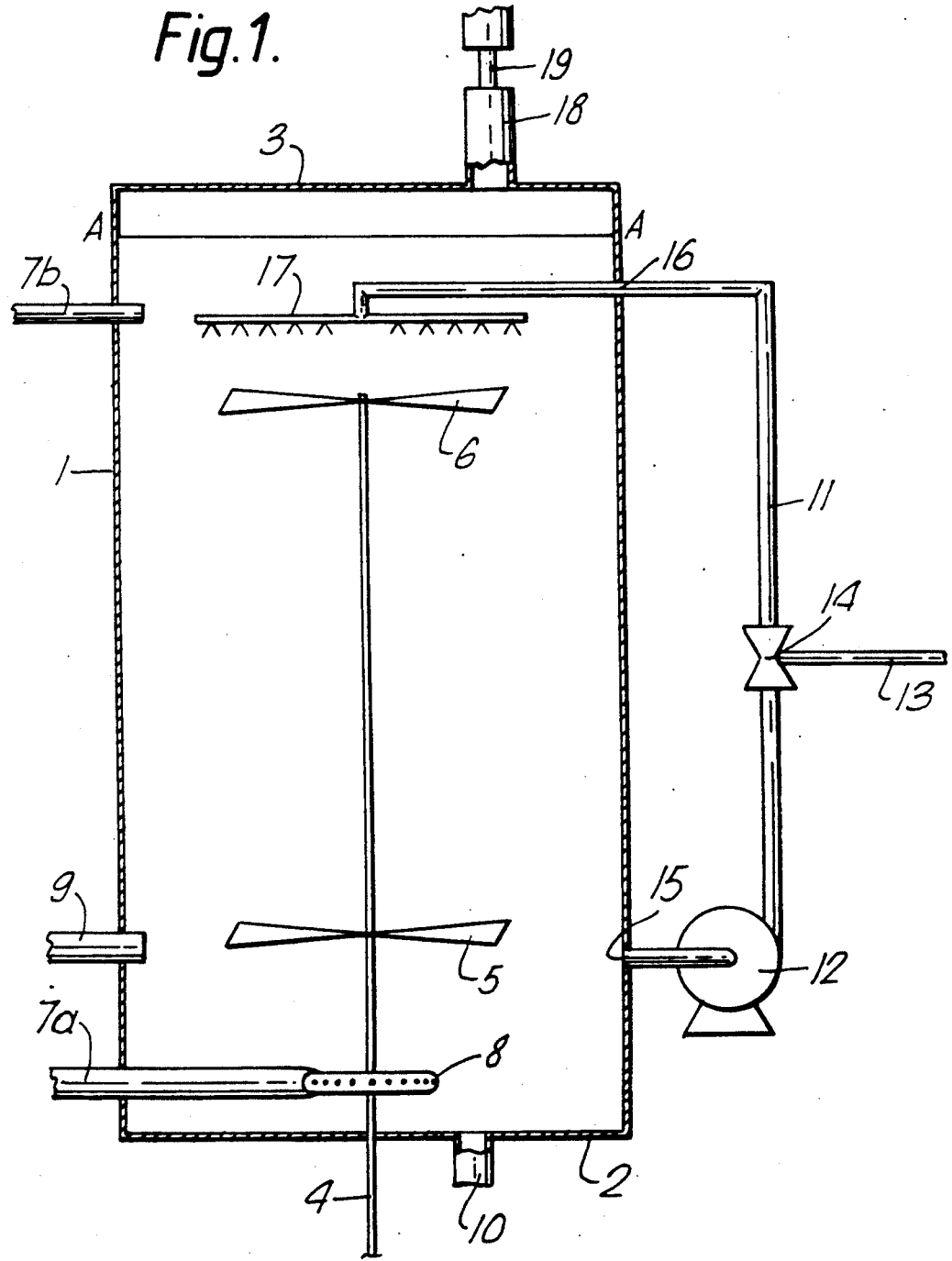

United States Patent [19]

Forsyth et al.

[11] Patent Number: 5,198,362
[45] Date of Patent: Mar. 30, 1993

[54] STERILE AEROBIC FERMENTATION PROCESS

[75] Inventors: Malcolm W. Forsyth, Cleveland; Stephen H. Hind, Derbyshire, both of England

[73] Assignee: Imperial Chemical Industries, PLC, London, England

[21] Appl. No.: 350,770

[22] Filed: May 11, 1989

[30] Foreign Application Priority Data

May 11, 1988 [GB] United Kingdom ............... 8811114

[51] Int. Cl.$^5$ .................... C12N 1/14; C12N 1/00; C12N 1/32
[52] U.S. Cl. .................................. 435/254; 435/243; 435/247; 435/315
[58] Field of Search ............... 435/243, 254, 247, 315

[56] References Cited

U.S. PATENT DOCUMENTS

| | | | |
|---|---|---|---|
| 2,822,319 | 2/1958 | Monod | 435/254 |
| 3,183,171 | 5/1965 | Schreiner | 435/254 |
| 3,749,646 | 7/1973 | Pirt | 435/254 |
| 4,204,042 | 5/1980 | Chelle | 435/243 |
| 4,782,024 | 11/1988 | Scott et al. | 435/247 |

FOREIGN PATENT DOCUMENTS

| | | |
|---|---|---|
| 0152201 | 8/1985 | European Pat. Off. . |
| 0152202 | 8/1985 | European Pat. Off. . |
| 2127747 | 12/1972 | Fed. Rep. of Germany . |
| 63-283570 | 11/1988 | Japan . |
| 1449889 | 9/1976 | United Kingdom . |
| 1572950 | 8/1980 | United Kingdom . |

OTHER PUBLICATIONS

Patent Abstracts of Japan, vol. 13, No. 107 (C-576) [3455k], 14th Mar. 1989; & JP-A-63 283 570 (DAIDO SANSO K.K.) 21-11-1988.

*Primary Examiner*—David M. Naff
*Assistant Examiner*—Mike Meller
*Attorney, Agent, or Firm*—Cushman, Darby & Cushman

[57] ABSTRACT

The present invention is directed to a fermentation process and a fermenter, wherein aeration is improved by injecting substantially pure oxygen into culture medium by outside the fermenter means including a venturi located outside the main body of the fermenter. The oxygen is preferably injected at the throat of the venturi. The volume of the culture medium outside the fermenter is not greater than 5% of the total volume of the culture medium. The invention is particularly suitable for use in the fermentation of viscous cultures, such as cultures of filamentous fungi.

5 Claims, 2 Drawing Sheets

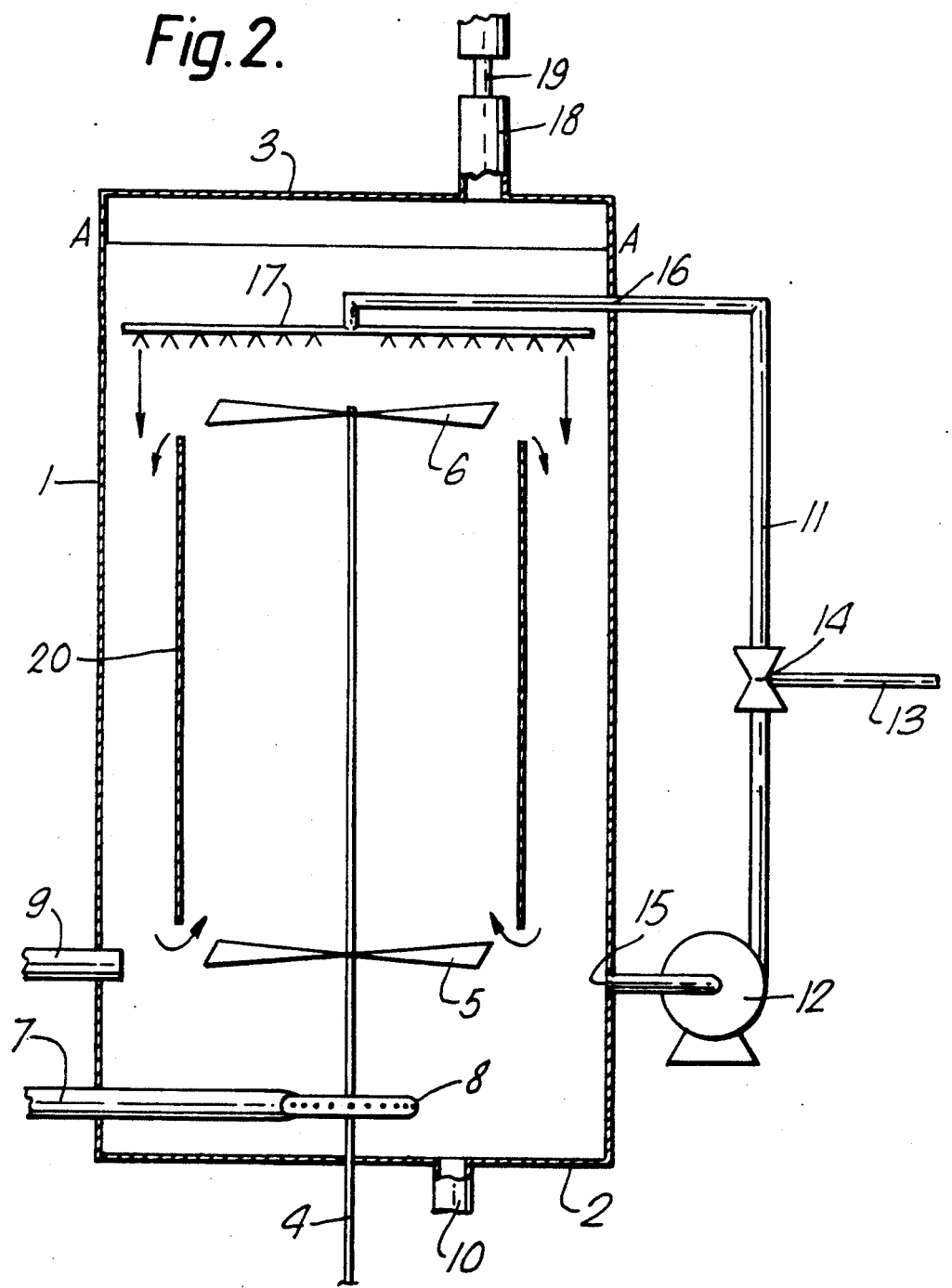

STERILE AEROBIC FERMENTATION PROCESS

This invention relates to a fermentation process and apparatus suitable in particular for fermenting viscous cultures.

In aerobic fermentations it is very important to have efficient aeration of the culture being fermented. This is difficult to achieve when the culture is viscous, e.g. when it contains a filamentous fungus, since it is difficult for the oxygen-containing gas supplied to the culture to break up into small bubbles which can efficiently enter the liquid phase.

According to the present invention we provide a process for the sterile fermentation of a mono-culture with mechanical stirring in a fermenter from which waste gas is continuously emitted wherein a portion of the culture continuously passes into a compartment outside the fermenter and substantially pure oxygen is injected into the culture outside the fermenter at the throat of a venturi or before the culture passes through a venturi, after injection the culture is continuously returned to the fermenter, the amount of culture outside the fermenter at any time being not greater than 5% of the total volume of the culture and wherein a volume of air and/or an inert gas greater than the volume of oxygen injected into the culture outside the fermenter, is injected into the culture in the fermenter.

Also according to the present invention, we provide a fermenter having in its main body mechanical stirring means, means for the addition of nutrients, means for the removal of product and means for the emission of waste gases wherein the fermenter comprises an external compartment provided with means for injecting substantially pure oxygen into culture contained therein at the throat of a venturi or before the culture passes through a venturi and connecting means are provided to enable a portion of a culture to pass from the main body of the fermenter into the compartment and thereafter to return to the main body, the volume of the compartment being such that not more than 5% of the total volume of a culture in the fermenter can be in the compartment at any time, and wherein the fermenter is provided with gas supplying means for injecting air and/or an inert gas at one or more locations to a culture in the main body thereof in a greater volume than the oxygen supplied to culture in the compartment.

The process of the invention can be a batch or a continuous process. When it is a continuous process the apparatus has means for the continuous addition of nutrients and for the continuous removal of product. For a batch or continuous process the apparatus has means for the continuous emission of waste gases, preferably at a velocity sufficient to maintain sterility by preventing the entrance of alien microorganisms to the apparatus.

Suitably the compartment is a pipe loop and the connecting means comprises openings in the wall of the main body of the fermenter to which the ends of the pipe loop are connected. Preferably culture is withdrawn through a lower opening towards the bottom end of the fermenter by a pump situated in the pipe loop and is returned to the fermenter through an upper opening towards the upper end of the fermenter. Substantially pure oxygen is suitably injected into culture flowing upwardly through it. Preferably oxygen is injected at the throat of the venturi device but it may also be injected into culture before it passes through the venturi. The venturi is preferably located in the pipe loop as near to the pump discharge as practicable.

When the oxygen is injected into the culture flowing through the compartment typically at the throat of a venturi, the resulting mixture of oxygen bubbles and liquid is subject to significant shear forces. This has the effect of reducing the size of the bubbles in the culture which is returned to the fermenter. Suitably the venturi system is similar to that described in European Patent Specifications 152201 and 152202.

The Process of the invention may be applied to any fermentation but is most useful in cases where the microorganism concerned is a filamentous fungus such as *Fusarium lateritium* or *Aspergillus niger*. It can however be applied to fermentations involving other microorganisms such as *Methylophilus methylotrophus*.

The proportion of the total culture which is in the compartment at any time should not be greater than 5% and is typically in the range 1% to 2%.

Air and/or an inert gas is injected into culture in the main body of the fermenter in a volume greater than the volume of oxygen injected into culture in the compartment. Typically it is injected at more than one location in the fermenter with most being injected near to the top. Suitably the total volume of air and/or inert gas is significantly greater than the volume of oxygen for instance sometimes up to 20 times the volume of oxygen depending upon the microorganism being cultured. The air and/or inert gas aids circulation of culture in the fermenter but its main purpose is to strip out from the culture the carbon dioxide which is produced during the fermentation. Unless it is removed the carbon dioxide can have a deleterious effect upon the fermentation. The air and/or inert gas carries the carbon dioxide upwardly through the culture to a space in the fermenter above the culture in which it disengages from the culture. The presence of inert gas reduces the pressure of carbon dioxide above the culture thereby reducing the amount of carbon dioxide which remains dissolved.

The gas disengaged from the culture is suitably allowed to escape from the fermenter through a pipe which is sufficiently narrow or which has a section which is sufficiently narrow to cause the gas to flow out with a velocity sufficient to prevent alien microorganisms from entering the fermenter against the flow of gas. This enables sterility to be maintained within the fermenter.

The use of substantially pure oxygen to aerate the culture enables the proportion of the main body of the fermenter which is occupied by culture to be increased as compared with a conventional fermentation process using air to aerate the culture. This is because the volume of gas supplied to the culture for its aeration is reduced since no inert nitrogen is added with the oxygen.

Circulation of the culture in the fermenter is mainly achieved using a mechanical stirring device. Circulation can be improved by providing the fermenter with internal partitions, in the case of a cylindrical fermenter with a cylindrical coaxial partition, to form an internal draught tube. This enables a regular flow pattern to be created with culture flowing downwardly near the outer wall of the fermenter and upwardly through the draught tube.

The invention leads to a number of advantages for fermentations (particularly those using viscous cultures) of which the following are especially important:

1. increased dry cell weight and hence increased productivity resulting from the easing of mass transfer limitations; and 2. An increased liquid inventory and hence higher production rates (e.g. 20% higher) resulting from the reduction in the gas headspace required in the fermenter as a result of lower volumes of gas passing through the fermenter. The invention is illustrated by the accompanying drawings.

In these:

FIG. 1 is a schematic diagram of a simple form of the fermenter of the invention; and FIG. 2 is a schematic diagram of an alternative, more sophisticated, form of the fermenter of the invention having an internal draught tube.

FIG. 1 shows a cylindrical fermenter having an outer wall 1, base 2 and top 3. It is equipped with a stirrer 4 having two paddles 5 and 6, forming an upward pumping agitator. Air and/or an inert gas can be admitted to the fermenter through pipe 7a and sparge ring 8 and/or pipe 7b whilst nutrients can be admitted through pipe 9 and culture removed through pipe 10. The compartment is a pipe-loop 11 having a pump 12, oxygen supply pipe 13 and venturi 14. Pipe-loop 11 is connected with the main body of the fermenter via openings 15 and 16. Oxygenated culture can be returned to the main body of the fermenter through nozzle system 17. Waste gases can escape from the fermenter through pipe 18 which has a narrow portion 19. The fermenter also has cooling means not shown in the drawings.

FIG. 2 shows a fermenter similar to that of FIG. 1 but containing a cylindrical internal partition 20 which forms a draught tube.

In operation the fermenters of FIGS. 1 and 2 are similar to one another. Air and/or an inert gas and nutrients are continuously supplied to the fermenter through pipes 7a, 7b and 9 respectively and culture is continuously removed from the fermenter through pipe 10. Culture is also continuously withdrawn from the fermenter through opening 15 into pipe loop 11 using pump 12. In pipe loop 11 pure oxygen is injected into the withdrawn culture through pipe 13, at the throat of the venturi device 14, where the oxygen in the culture is dispersed into fine bubbles. The oxygenated culture is returned to the culture in the main body of the fermenter through opening 16 and nozzle system 17. The air and/or inert gas which is admitted to the main body of the fermenter through pipe 7a and sparge ring 8 rises to the surface A—A of the culture carrying with it carbon dioxide produced during the fermentation. The air and/or inert gas admitted to the main body of the fermenter through pipe 7b fills the space above the surface A—A and reduces the carbon dioxide partial pressure to a low level. At the surface A—A gas disengages from the culture and escapes to the atmosphere through pipe 18. In pipe 18 escaping waste gas is accelerated by passing through narrow portion 19 to a speed which prevents alien microorganisms from entering the fermenter against the gas flow. When partition 20 is present a regular flow pattern is created within the fermenter with culture rising in the central part within the internal draught tube created by 20 aided by the air flow from sparge ring 8, and falling near the side 1 of the fermenter outside the draught tube, aided by the downward flow of oxygenated culture from the nozzle system 17.

The invention is further illustrated by the following Examples:

EXAMPLE 1

A culture of *Fusarium lateritium* was fermented by continuous culture in the fermenter illustrated in FIG. 1 and described above. The culture medium had the following composition:

| Medium | |
|---|---|
| Glucose | 30 g/l feed |
| Trace metals P, Fe, Ca, Mg, K, Mn, Cu, Zn present | |
| P, K | 500–1000 ppm |
| Mg | 100 ppm |
| Ca | 25 ppm |
| Fe, Mn, Cu, Zn | <5 ppm |

The operating conditions for the fermentation were as follows:-

| | |
|---|---|
| pH | 6.0 |
| temperature | 29.5° C. |
| overpressure | 5 psig |
| vessel volume | 250 L |
| pump flow rate | 8 m$^3$/h (estimated) |
| pump power draw | 1800 W (estimated) |
| agitation rate | 200 rpm |
| agitation power draw | 240 W |
| inert gas (nitrogen) purge rate (total) | 6.6 Nm$^3$/h - 10% of this was through the bulk and the remainder through the head space. |

The fermentation was continued for 12 hours after which time the following fermentation performance characteristics were achieved:

| | |
|---|---|
| dry cell weight | 25 g/l |
| dilution rate | 0.12 /h |
| productivity | 3 g/l/h |
| oxygen feed | 0.92 kg/h |
| oxygen demand | 0.55 kg/h |
| oxygen utilization efficiency | 60% |
| carbon conversion efficiency | 62% |
| cell yield on carbon source (glucose) | 60% |

In a further experiment using the same fermenter, culture and conditions the following performances were achieved when substantially pure oxygen was used and when it was not used, i.e. operating under conventional conditions of aeration and agitation:

| | Oxygen used | Oxygen not used |
|---|---|---|
| Dry cell weight (g/l) | 29.4 | 29.0 |
| Productivity (g/lh) | 4.8 | 4.3 |
| Instantaneous growth rate (h$^{-1}$) | 0.26 | 0.22 |

From these results it can be seen that the use of the process of the invention can lead to a high productivity fermentation.

EXAMPLE 2

A culture of *Methylophilus methylotrophus* was fermented by continuous culture in the fermenter illustrated in FIG. 1 and described above. In this experiment, the liquid inventory was maximised first when running the fermenter in the conventional manner (oxygen requirement supplied by agitation and aeration with the pump loop shut off), and second when using the pumped loop to supply oxygenated culture and mixing.

The maximum liquid inventory was deemed to be that level at which the fermentation could be controlled steadily without the fermenter contents foaming out of the top of the vessel.

The operating conditions for the first and second cases are set out in the following Table:

TABLE

| Parameter | Agitation/aeration operation alone | Pumped loop operation |
|---|---|---|
| pH | 6.6 | 6.6 |
| Temperature | 30° C. | 39° C. |
| Overpressure | 15 psig | 5 psig |
| Pump flow rate | — | 10.5 m$^3$/h (estimate) |
| Pump power draw | — | 1200–1600 W (estimate) |
| Agitation rate | 350 rpm | 160 rpm |
| Agitator power draw | 1250 W | 400 W |
| Air flow rate | 18 Nm$^3$/h | — |
| N$_2$ purge rate | — | 7.6 Nm$^3$/h |
| Dilution rate | 0.1/h | 0.1/h |
| Max. liquid inventory | 200 liters | 240 liters |
| Vessel volume | 250 liters | 250 liters |
| % utilisation of vessel volume | 80% | 96% |

Both modes of operations produced similar fermentation performance, viz

| Dry cell weight | 18 g/l |
|---|---|
| Carbon conversion efficiency | 50% |
| Cell yield on methanol | 32% |

From these results, it is clear that significant increases in utilisation of available volume, can be achieved. In this case, utilisation of available volume was raised by 20%, giving a 20% increase in production rate from the original vessel. No detrimental effect on fermentation performance was observed in achieving this increase.

We claim:

1. A process for the sterile fermentation of a monoculture with mechanical stirring in a fermenter from which waste gas is continuously emitted, comprising the steps of continuously passing a portion of the culture into a compartment outside the fermenter and injecting substantially pure oxygen into the culture outside the fermenter at the throat of a venturi or before the culture passes through a venturi; after injection, continuously returning the culture to the fermenter, the amount of culture outside the fermenter at any time being not greater than 5% of the total volume of the culture; and injecting into the culture in the fermenter, a volume of air and an inert gas greater than the volume of oxygen injected into the culture outside the fermenter.

2. A process according to claim 1 wherein substantially pure oxygen is injected into upwardly flowing culture outside the fermenter.

3. A process according to claim 1 wherein substantially pure oxygen is injected into the culture outside the fermenter at the throat of the venturi.

4. A process according to claim 1 wherein the culture is a culture of a filamentous fungus.

5. A process for the sterile fermentation of a monoculture with mechanical stirring in a fermenter from which waste gas is continuously emitted, comprising the steps of continuously passing a portion of the culture into a compartment outside the fermenter and injecting substantially pure oxygen into the culture outside the fermenter at the throat of a venturi or before the culture passes through a venturi; after injection, continuously returning the culture to the fermenter, the amount of culture outside the fermenter at any time being not greater than 5% of the total volume of the culture; and injecting into the culture in the fermenter, a volume of air or an inert gas greater than the volume of oxygen injected into the culture outside the fermenter.

* * * * *